(12) United States Patent
Haveri et al.

(10) Patent No.: US 8,746,090 B2
(45) Date of Patent: Jun. 10, 2014

(54) ARRANGEMENT FOR FASTENING SENSOR TO FACE OF SUBJECT AND MEASURING ASSEMBLY

(75) Inventors: Heikki Haveri, Huhmari (FI); Kristina Leppala, Vantaa (FI)

(73) Assignee: General Electric Company, Schenectady, NY (US)

(*) Notice: Subject to any disclaimer, the term of this patent is extended or adjusted under 35 U.S.C. 154(b) by 173 days.

(21) Appl. No.: 13/017,086

(22) Filed: Jan. 31, 2011

(65) Prior Publication Data

US 2011/0197689 A1 Aug. 18, 2011

(30) Foreign Application Priority Data

Feb. 18, 2010 (EP) .................................... 10153965

(51) Int. Cl.
*A61B 5/087* (2006.01)
(52) U.S. Cl.
USPC ......................................................... 73/866.5
(58) Field of Classification Search
None
See application file for complete search history.

(56) References Cited

U.S. PATENT DOCUMENTS

| | | | |
|---|---|---|---|
| 3,658,054 A * | 4/1972 | Iberall | 600/485 |
| 5,284,469 A | 2/1994 | Jasen et al. | |
| 5,983,129 A * | 11/1999 | Cowan et al. | 600/544 |
| 7,087,027 B2 * | 8/2006 | Page | 600/537 |
| 7,445,602 B2 * | 11/2008 | Yamamori et al. | 600/532 |
| 2003/0199780 A1 | 10/2003 | Page | |
| 2009/0088657 A1 * | 4/2009 | Yamamori et al. | 600/532 |
| 2009/0105605 A1 * | 4/2009 | Abreu | 600/549 |
| 2009/0255535 A1 * | 10/2009 | Kanzer | 128/206.14 |

FOREIGN PATENT DOCUMENTS

| | | |
|---|---|---|
| WO | 2008/019294 A2 | 2/2008 |
| WO | 2009/109005 A1 | 9/2009 |

OTHER PUBLICATIONS

Search Report and Written Opinion from EP Application No. 10153965.8 dated Sep. 6, 2010.
Unofficial translation of Search Report from CN Application No. 2011100440262 on Nov. 22, 2013.
Office Action issued in connection with EP Application No. 10153965.8 on Aug. 30, 2012.

* cited by examiner

*Primary Examiner* — Robert R Raevis
(74) *Attorney, Agent, or Firm* — Global Patent Operation; Marc A. Vivenzio

(57) ABSTRACT

An arrangement for fastening at least one sensor to a face of a subject to acquire a signal indicative of one or more patient physiological parameter is disclosed herein. The arrangement includes a sensor holder for placing the sensor and having at least one fixing point. The arrangement also includes at least one ribbon being stretching for fastening the sensor holder by means of the at least one fixing point to an ear of the subject. Also a measuring assembly is disclosed herein.

18 Claims, 3 Drawing Sheets

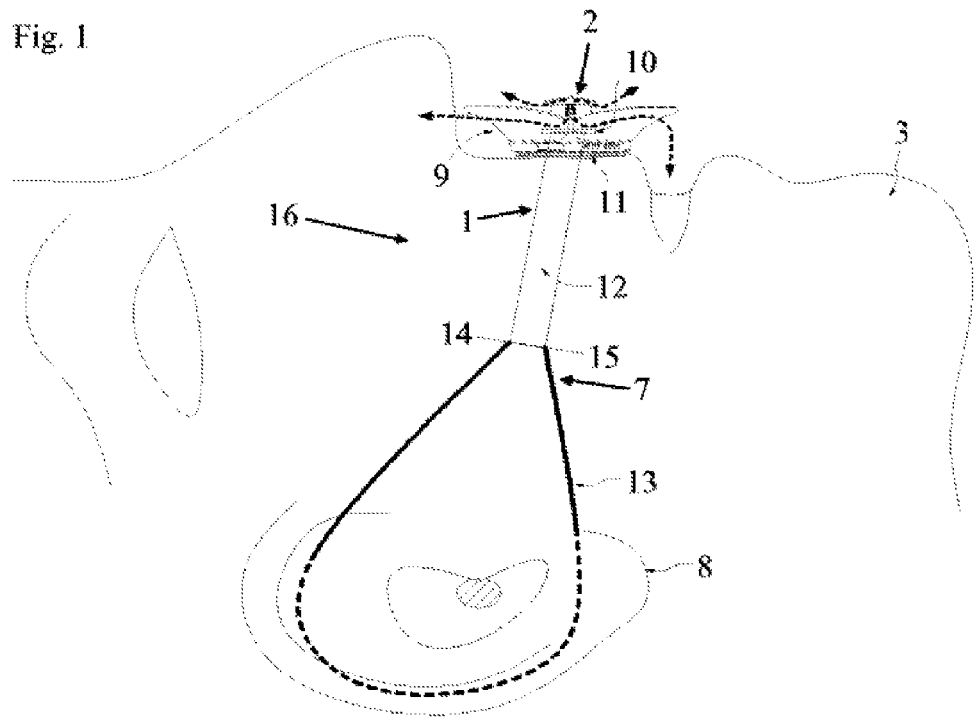

ARRANGEMENT FOR FASTENING SENSOR TO FACE OF SUBJECT AND MEASURING ASSEMBLY

BACKGROUND OF THE INVENTION

This disclosure relates generally to an arrangement for fastening at least one sensor on a face of a subject to acquire one or more signals indicative of patient physiological parameter and also relates to a measuring assembly.

There is a need for placing sensors on a patient's face for measuring signals indicative of the patient's physiological condition. Sensors may acquire signals proportional to for example a body temperature, breathing gas concentration etc. One good example of a sensor placed is a respiration flow sensor used for measuring a breathing gas flow through a mouth and nose. Such sensors are used in hospital wards, home- or elderly care or in a sleep laboratory, where there is a need to detect a breathing deficiency or even apnea, caused by for example opiates, other medicine, an obstruction in the airways or as a consequence of a neurological disease or trauma.

Existing respiration sensors are usually placed on the patient's face, on or near by the patient's mouth or on the upper lip, between the mouth and the nose. Some small and light sensors are commonly attached on the face with a tape or similarly gluing. Some sensors are attached on a face with a rubber band type string going around the patient's neck or occiput. It is obvious that if such sensors come off, as the glue looses its grip on the skin or if the rubber band snaps, there is a high risk that the sensor enters the patient's upper airways or trachea causing choking and death. Partly for that reason some sensors are attached with a helmet type rubber net dressed on the patient's whole head, but such configuration is uncomfortable to wear as the helmet type rubber net squeezes and presses the face and the head.

Respiration sensors based on measuring pressure change caused by the flow of the breathing gas usually comprise voluminous pressure sensors and electronics due to they have been placed further away from patients face into a remote unit, such as a patient monitor or similar, and only the tubing used to sense and transfer the pressure change to the remote unit is placed on the patient's face. Such tubing is usually suspended under the nose, cannulas entering the nasal cavities, extending there on ears and continuing around the head to the remote unit or alternatively continuing from ears to the chest over the jaws. Tubes are commonly made of plastics and they are rather inflexible and uncomfortable to wear, furthermore the cannulas irritate the hawse pipes and are easily torn off by the patient.

The attachment and placement of existing configurations, such as described above, is insufficient in practice. It is common in hospital to use a tape to attach above sensors on patients face to prevent them to end up in to an incorrect place.

BRIEF DESCRIPTION OF THE INVENTION

The above-mentioned shortcomings, disadvantages and problems are addressed herein which will be understood by reading and understanding the following specification.

In an embodiment, an arrangement for fastening at least one sensor to a face of a subject to acquire a signal indicative of one or more patient physiological parameter includes a sensor holder for placing the sensor and having at least one fixing point. The arrangement for fastening at least one sensor to a face of a subject also includes at least one ribbon being stretching for fastening the sensor holder by means of the at least one fixing point to an ear of the subject.

In another embodiment, a measuring assembly includes a sensor for fastening to a face of a subject to acquire a signal indicative of one or more patient physiological parameter and a sensor holder for placing the sensor and having at least one fixing point. The measuring assembly also includes at least one ribbon being stretching for fastening the at least one fixing point of the sensor holder to an ear of the subject.

In yet another embodiment, an arrangement for fastening at least one sensor to a face of a subject to acquire a signal indicative of one or more patient physiological parameter includes a sensor holder for placing the sensor and having at least one fixing point. The arrangement for fastening at least one sensor to a face of a subject also includes at least two ribbons being stretching for fastening the sensor holder by means of the at least one fixing point to both ears of the subject.

Various other features. Objects, and advantages of the invention will be made apparent to those skilled in art from the accompanying drawings and detailed description thereof.

BRIEF DESCRIPTION OF THE DRAWINGS

FIG. 1 is a side view of the an arrangement for fastening a sensor on a face of a subject;

FIG. 2 is a cross sectional view of a sensor holder for placing the sensor from three different projections;

DETAILED DESCRIPTION OF THE INVENTION

Figure 3:
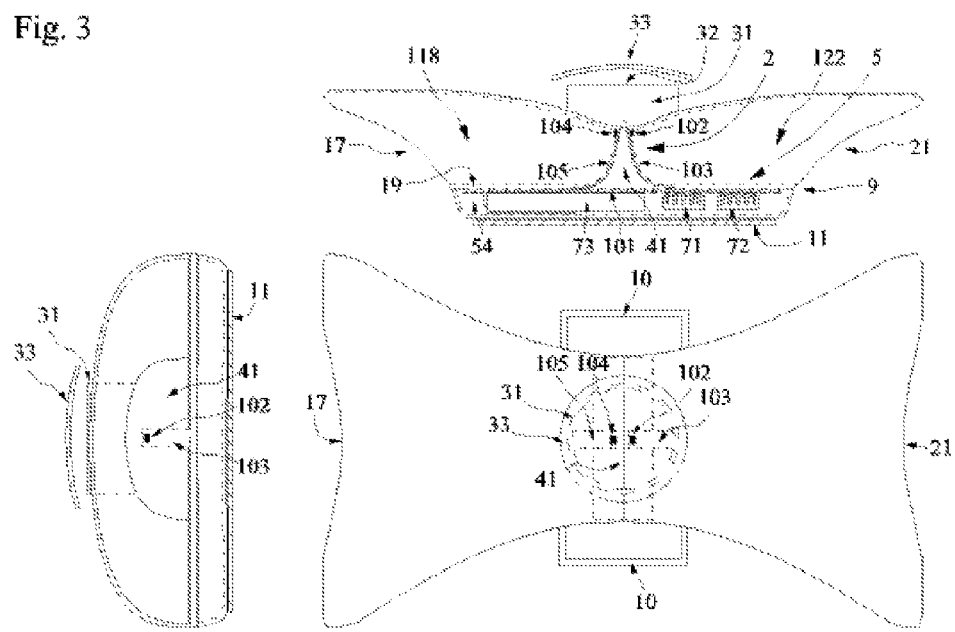
FIG. 3 is a cross sectional view of a second embodiment of the sensor holder for placing the sensor from three different projections.
Figure 4:
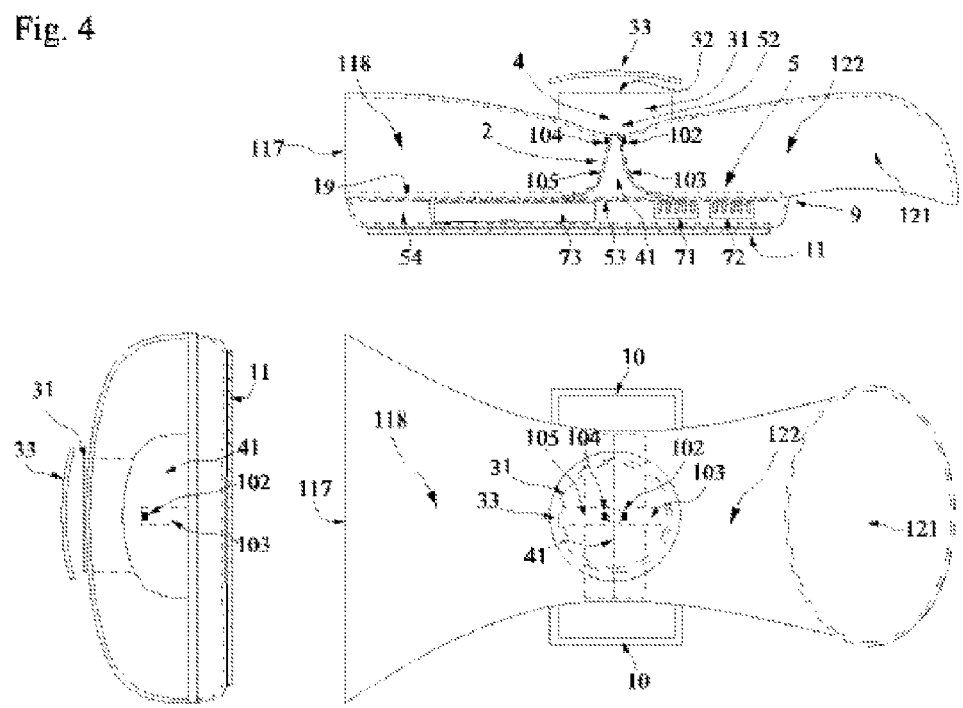
FIG. 4 is a cross sectional view of a third embodiment of the sensor holder for placing the sensor from three different projections.

FIG. 1 shows an arrangement 1 for fastening at least one sensor 2 to a face of a subject 3 to acquire a signal indicative of a patient physiological parameter such as respiratory functions. The sensor 2 typically comprises as shown in FIG. 2 at least one detector 4 to acquire a signal being indicative of at least one physiological parameter. Also the sensor 2 may comprise a sensor electronics 5 for signal processing as shown in FIGS. 2, 3 and 4. The sensor 2 can be used for instance to acquire a signal indicative of a flow or a relative flow or a respiration rate of a respiration gas flow through a nose, a mouth or the both at the same time and can also detect apnea. The measurement may be based on measuring a thermal component of the respiration gas flow with at least one detector 4, such as a thermistor as shown in FIG. 2, for detecting a subject breathing. Thermal changes of the respiration gas flowing by the thermistor change the detector's resistance, which is converted into a continuous electrical signal. The amplitude of the signal is proportional to the flow rate of the breathing gas and the frequency is proportional to the respiration rate (RR). These signals can also be used for detecting apnea. Also it is possible to equip the sensor 1 with another detector to acquire a signal indicative of one or more component or their concentration in the respiration gas.

The arrangement 1 comprises at least one ribbon 7, which is stretching, for fastening the sensor 2 to an ear 8 of the subject 3 when the sensor 2 is placed on a skin below a nose but above the subject's upper lip or mouth. The arrangement 1 also comprises a sensor holder 9 having at least one fixing point 10 such as a handle for the stretching ribbon 7. Advantageously there are two fixing points 10 locating on both sides of the sensor holder, both fixing points being connectable to separate ribbons, which can be fastened to different ears. Irrespective of the number of fixing points there can be for example two ribbons for each fixing point, but which ribbons can form a single ribbon or two different ribbons when untied from the fixing point. The ribbon extending from the fixing point is tied to this fixing point. The stretching ribbon 7 extends around the subject's ear 8. In this case the sensor 2 may be detachably fastened to the sensor holder 9. Also the sensor holder 9 with at least one fixing point 10 may be part of the sensor 2, in which case the stretching ribbon 7 can be fastened to the at least one fixing point of the sensor holder 9. If desired the sensor holder may be also glued on with a sticker 11 located on the bottom of the sensor holder 9.

The stretching ribbon 7 is used to eliminate the risk that the sensor 2 enters the subject's respiratory system, mainly through the mouth and causes patient to choke, if the sticker 11 looses its grip on the upper lip for some reason.

The stretching ribbons 7 fastened to both ears 8 also tighten the sensor holder 9 with the sensor 2 against the subject's upper lip especially in case no sticker 11 is used, ensuring that the sensor stays in the correct place on the upper lip, between the nose and the mouth. The sticker 11 can be used to improve the sensor grip.

The ribbon can be partly stretching and partly substantially inelastic. It does not necessarily be stretching for its whole length. So the ribbon can comprise both stretching and inelastic parts. Advantageously the first part 12 of the ribbon 7 may be inelastic, lying against patient's cheeks, can be made wider than the second part to prevent the ribbon to plunge into the skin irritating and/or harming the patient. The second part 13 of the ribbon may be stretching, extending around the subject's ear or ears 8, may be made of a strip, which cross section is round, preventing the strip to irritate and/or harm the background of the ear. Thus the first part 12 of the ribbon, which is substantially inelastic, may join the second part 13 of the ribbon to the fixing point of the sensor holder 9. However, both the first part 12 and the second part 13 may be made of soft cotton or similar non-allergic, non-irritating material and at least one of the first part 12 and the second part 13 also includes a stretching function that pulls the sensor 2 against the upper lip of the subject.

If the sticker 11 looses its grip on the upper lip or if there is no sticker, stretching ribbons 7 behind the ears 8 prevent the sensor 2 to enter into the respiratory system. Furthermore, if one of the stretching ribbons 7 comes loose at the same time as the sticker looses its grip on the upper lip, the sensor is ejected aside from the upper lip by the pulling force of the remaining ribbon 7 preventing the sensor to enter the respiratory system such as the mouth of the subject.

In FIG. 1 the ribbon 7 encircles the ear 8 forming a loop when both its first end 14 and second end 15 are directly or indirectly connected to the fixing point 10 of the sensor holder 9. Actually in FIG. 1 when the ribbon comprises of two parts, then its first end 14 and the second end 15 of the second part 13 can be directly or indirectly connected to the fixing point 10 of the sensor holder 9. In case the ribbon 7 comprises the first part 12 and the second part 13 joined together as shown in FIG. 1, the second part 13 having the first end 14 and the second end 15 encircles the ear and the first and second ends connect to the first part 12 of the ribbon 7 in which case the second part 13 with the first end 14 and the second end 15 is indirectly connected to the sensor holder 9. The embodiment, where the ribbon 7 is arranged around the ear 8, is believed to be secure even without the sticker 11. It is also possible to use such a ribbon 7 which is stiff enough to encircle only partly the ear but which leans on the ear bending behind the ear. In this case it is better to have a stretching part between the bending part and the sensor holder 9.

Also a measuring assembly 16 is shown in FIG. 1 comprising the sensor 2, the sensor holder 9 with at least one fixing point 10 and at least one stretching ribbon 7 for fastening the at least one fixing point of the sensor holder to an ear of the subject. These different features have been introduced hereinbefore and hereinafter.

FIG. 2 shows three different projections of the sensor holder 9 having the sensor 2 for measuring the respiration. The sensor holder 9 may be only a substrate for receiving the sensor, which combination of the sensor holder 9 and the sensor 2 may form an integral structure or may be detachable from each other. The sensor holder 9 can also be a housing as shown in FIG. 2 having a place inside the housing for the sensor 2. Also in this case the sensor holder 9 and the sensor 2 can form an integral structure or be detachable from each other.

The sensor holder shown in FIG. 2 comprises a first port 17 opening towards the nose, a second port 21 opening towards the mouth and at least one additional port 31, located between the first port 17 and the second port 21 and it preferably opens away from the subject. The sticker 11 is in this embodiment opposite to the opening direction of the additional port 31. The first ports 17 and the second port 21 have symmetrical construction relative to the additional port 31 so that the sensor holder 1 can be placed either way between the nose and the mouth. The first port 17 and the second port 21 connect to the additional port 31 through continuous cavities, where the respiratory air can flow between the subject's respiratory system and the ambient. Thus the first port 17 allows the respiration gas flow into the first cavity 18 and the second port 21 allows the respiration gas flow into the second cavity 22 in case the additional port 31 is only removing the respiration gas and correspondingly the first port 17 allows only the respiration gas flow out from the first cavity 18 and the second port 21 allows only the respiration gas flow out from the second cavity 22 in case the additional port 31 is allowing the respiration gas flow into the first cavity 18 and the second cavity 22. Instead of using one additional port 31 there may be two or more additional ports, one for the first cavity 18 and another for the second cavity 22.

As shown in FIG. 2 the first cavity 18 and the second cavity 22 are against one another. The first cavity 18, extending from the nose to the additional port 31, is for the respiratory gas flowing between the nose and the ambient as shown with dashed lines in FIG. 1, whereas the second cavity 22, extending from the mouth to the additional port 31, is for the respiratory gas flowing between the mouth and the ambient as also shown with dashed lines in FIG. 1. Inside the sensor holder 9, in a cross section of cavities 18, 22, on a bottom plate 19, in the middle of the additional port 31, is a flow guide 41 that directs the gas flow from either of the cavities 18 and/or 22 towards an opening 32 of the additional port 31 or vice versa. The flow guide 41 turns the respiration gas flow direction of the first cavity 18 and the second cavity 22 meaning that also the first cavity and the second cavity are turned 30-90 degrees, more specifically 45-90 degrees, or even more specifically 80-90 degrees to achieve the at least one additional port 31. Furthermore the flow guide 41 prevents the respiration gas to flow between the cavities 18 and 22, in other words between the nose and the mouth, that would otherwise cause subject to re-breath gases and decrease the gas exchange in the lungs.

As explained hereinbefore the sensor 2 comprises at least one detector 4 which is in this example used for indicating breathing function being placed on the at least one additional port 31 or being close by the additional port 31. In the embodiment shown in FIG. 2 only one detector 4 for indicating breathing function is enough, but naturally there can be more than one. The detector 4 can be fixed on a strip 52 branching from the sensor electronics 5 comprising a flexible electronic circuit board 53 being part of the sensor and locating inside an intermediate space 54 of the sensor holder 9 formed between the bottom plate 19 and a lower part of the sensor holder 9. The sensor holder 9 is preferably made of recyclable plastic or similar material that can be easily and inexpensively produced, has low unecological impact and has a low thermal conductivity to achieve a good measurement sensitiveness. The strip 52 extends through an opening in the bottom plate 19, from the intermediate space 54, into one of the first cavity 18 and the second cavity 22 as shown in FIG. 2 and bends against the flow guide 41, so that the detector 4 is located close into the middle of the tip 42 of the flow guide 41, in to the middle of the gas flow directed by the flow guide 41 inside the additional port 31.

The detector 4 for indicating breathing functions, which may be the thermistor, senses the thermal component of the respiratory gas flowing past the detector 4, between the respiratory system and the ambient, which changes the detector 4 resistance proportional to the temperature change of the flowing gas, which is then transformed into a continuous electrical signal. When the subject breathes out the warm breathing gas coming from the respiratory system warms up the detector 4 increasing/decreasing the resistance of PTC/NTC type breathing detector, whereas the subject breathes in the cooler air from the ambient it cools down the detector decreasing/increasing the resistance of PTC/NTC type breathing detector. The thermal connection between the detector 4 and the surrounding mechanics has to be low to ensure high sensitivity and first response time to temperature changes caused by the flowing respiratory air. To increase the sensitiveness, the cross sectional shape of the first cavity 18 and the second cavity 22 decrease from the openings of first port 17 and the second port 21 towards the flow guide 41 and the additional port 31, A cross-sectional area of the at least one additional port 31 may be less than 10% of a combined cross-sectional area of the first port 17 and the second port 21, more specifically less than 20% or even more specifically less than 50% of the combined cross-sectional area of the first port and the second port. This increases the flow speed of the respiratory gas along the first cavity 18 and the second cavity 22 to its maximum speed as it enters the additional port 31 and passes the detector 4 placed close to the narrowest cross sectional area of the whole respiratory gas flow bath. The increased speed of the respiratory gas flow increases the heating/cooling effect of the gas flowing past the detector 4 in turn increasing the sensitiveness of the respiratory gas flow measurement.

The additional port 31 is covered with a hood 33, or a similar protective construction, to prevent any disturbing ambient airflows, such as airflow from the air conditioner etc., to enter straight in to the additional port 31 and to the detector 4 that may cause error or even destroy the measurement of respiratory gas flow.

The detector 4 electrically connects to the sensor electronics 5 located on the bottom side of the flexible electronics circuit board 53 inside the intermediate space 54. The sensor electronics comprise an amplifier 71 for amplifying the voltage signal from the detector 4, a processor 72 for converting the amplified analog voltage signal into a digital form and for processing the digital data into values of RR and real time waveform data. The processor 72 may even comprise radio frequency transceiver, or similar, for wireless communication between the host device, such as patient monitor (not shown in Figure) that could show the real time waveform and the value of RR, as well as apnea and other alarms on its display. The operating power for the wireless respiration sensor 2, as described previously, can be delivered from an electrical battery 73, such as 3V, Li-battery made by the company Varta Consumer Batteries, which diameter is 12.5 mm and the height is 1.6 mm.

It is obvious that the sensor 2 can be connected to the patient monitor or similar host through electrical cable as well (not shown in Figure). In this case it is reasonable to leave out most of the electronics and the electrical battery, such as processor etc. from the sensor 2 and place them into the host device.

In the sleep laboratory, where subjects suffering from different type of sleep apnea are examined, it is sometimes important to know if the subject is breathing through the nose or the mouth. FIG. 3 shows a sensor 2 to acquire a signal indicative of a patient physiological parameter such as respiratory functions, which is slightly modified from the sensor shown in FIG. 2, comprising the sensor electronics 5 which is an alternative electronic flex circuit board 101. In the circuit 101, the detector 102 to acquire a signal being indicative of at least one physiological parameter, such as breathing functions, is placed on a strip 103 that bends against the wall of the flow guide 41 extending only on the side of the wall. The detector 102 can only acquire a signal indicative of the respiration gas flowing through the second cavity 122 which signal is in this specific case the thermal component of the respiratory gas flow between the mouth and the ambient. Similarly, the detector 104 is placed on a strip 105 that bends against the wall on the adjacent side of the flow guide 41 in regard to the detector 102, also extending only on the side of the wall. The detector 104 can only acquire a signal indicative of the respiration gas flowing through the first cavity 118 which signal is in this specific case the thermal component of the respiratory gas flow between the nose and the ambient. In this embodiment the sensor holder 9 is equipped with two additional ports 31 and both additional ports are equipped with the detector 102, 104, one detector 104 acquiring the signal indicative of the respiration gas coming from the nose or to the nose along the first cavity 118 and another detector 102 acquiring the signal indicative of the respiration gas coming from the mouth or to the mouth along the second cavity 122. This construction increases the cost of the disposable respiration sensor 2 or the sensor holder 9 compared to the construction shown in FIG. 2, but it enables the measurement of thermal components of respiratory gas flows between the mouth and the ambient as well as the nose and the ambient separately.

The construction of the sensor holder 9 and the sensor 2 described above and shown in FIGS. 2 and 3 is position sensitive and can be positioned either way in regard to the nose and the mouth, whereas it is desirable to be placed only one way to get correct flow data from the nose and the mouth. To help the right positioning, the sensor holder 9 may have pictures or text on its top surface showing the user, which way the sensor should be placed in regard to the nose and the mouth. However, there still remains a high possibility for user errors that the sensor holder 9 with the sensor 2 is positioned incorrectly, which in turn causes the flow data to be mixed crosswise between the nose and the mouth.

FIG. 4 shows a further embodiment, which solves the problem described above and shown in FIG. 3. The construction is almost the same as in the FIG. 3, except the second port 121 towards the mouth is a trough-like guide having a shape of a spoon or similar. The spoon like second port 121 efficiently directs the respiratory gas flow from the mouth towards the second cavity 122, where it continues to flow out from the additional port 31. Similarly, the first port 117 towards the nose has a straight opening that efficiently directs the respiratory gas flow from the nose towards the first cavity 118, continuing the flow out through the additional port 31. With this construction it is safe to mate the detector 104 with the first port 117 for measuring the respiratory gas flow between the nose and the ambient and similarly to mate the detector 102 with the second port 121 for measuring the respiratory gas flow between the mouth and the ambient since, if the sensor holder 9 with the sensor is placed on the subject's upper lip no that the first port 117 is towards the mouth, the opening of the second port 121 is closed by the upper lip. This prevents the respiratory gas to flow between the nose and the ambient, when the sensor holder 9 with the sensor 2 is placed incorrectly, causing the sensor to show zero or a constant value, which in turn can be alarmed for the user.

The detector 4 may comprise a gas analyzer measuring, for example the gas component or the gas concentration of $CO_2$ or $O_2$ from the breathing gas, or similar. However, the size of the gas analyzer has to be small enough to fit the construction and to be unnoticeable for the subject. Chemical cells, gas absorption at infrared wavelengths etc. are potential technologies already available to fit the sensor 2.

Figure 5:
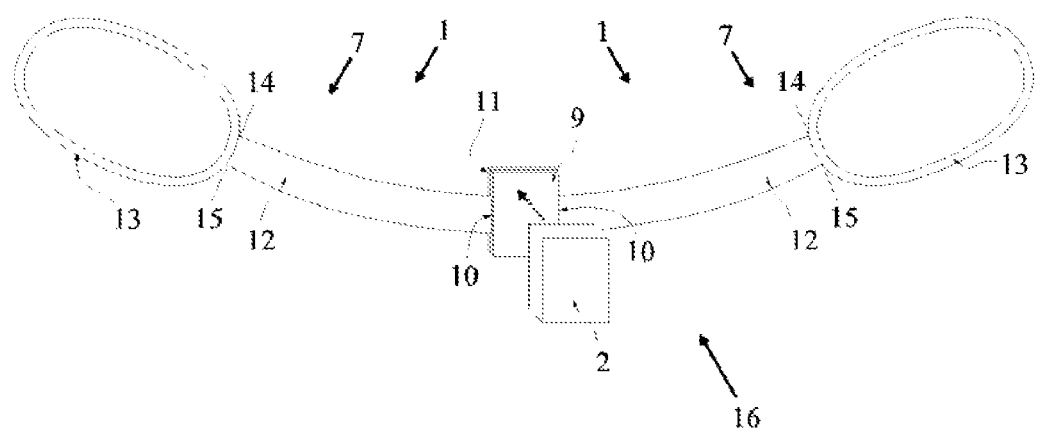
FIG. 5 is a front view of a fourth embodiment of the sensor holder for placing the sensor.

FIG. 5 shows an arrangement 1 for fastening at least one sensor 2 to a face of a subject to acquire a signal indicative of a patient physiological parameter such as respiratory functions. The arrangement 1 comprises at least one ribbon 7, which is stretching, for fastening the sensor 2 to an ear of the subject, when the sensor 2 is placed on a skin below a nose but above the subject's upper lip or mouth. The arrangement 1 also comprises a sensor holder 9 having at least one fixing point 10, such as a handle for the stretching ribbon 7 as shown in FIGS. 2, 3 and 4, or the coupling of stretching ribbon 7 and sensor holder 9 may be jointless. Advantageously there are two fixing points 10 on both sides of the sensor holder 9, which can be fastened to different ears. The stretching ribbon 7 extends around the subject's ear. In this case the sensor 2 may be detachably fastened to the sensor holder 9. The sensor 2 may comprise at least one a detector to acquire a signal being indicative of at least one physiological parameter as shown in FIGS. 2, 3 and 4. Also the sensor 2 may comprise a sensor electronics for signal processing as shown in FIGS. 2, 3 and 4. The sensor 2 may be used for instance to acquire a signal indicative of for example a respiratory gas flow, respiratory gas concentration, body temperature etc. If desired the sensor holder 9 may be also glued on with a sticker 11 located on the bottom of the sensor holder 9. The arrangement 1 may be constructed of inexpensive materials that can be disposed, as they are in straight contact with the patient, which is a benefit in minimizing the risk of cross contaminating between patients. The sensor 2 may comprise more expensive electronics that may be reusable. Also the whole measuring assembly 16 comprising the sensor holder 9, the sensor 2 and at least one ribbon 7 is shown in FIG. 5.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. An arrangement for fastening at least one sensor to a face of a subject to acquire a signal indicative of one or more patient physiological parameter, the arrangement comprising:
    a sensor holder configured to hold the at least one sensor, wherein the at least one sensor is detachable from the sensor holder; and
    at least one fastener connected to the sensor holder and configured to fasten the sensor holder to an ear of the subject, the at least one fastener comprising a first length that is substantially inelastic and a second length that is stretchable.

2. The arrangement according to claim 1, wherein the second length of the at least one fastener is configured to encircle the ear of the subject and to form a loop.

3. The arrangement according to claim 1, further comprising a sticker configured to glue the sensor holder on a skin of the subject below a nose but above the subject's upper lip or mouth.

4. The arrangement according to claim 1, wherein the sensor holder further comprises:
    a first cavity comprising a first port and is configured to allow a first respiration gas flow;
    a second cavity comprising a second port and is configured to allow a second respiration gas flow; and
    at least one additional port configured to remove the respiration gas flows coming from the first cavity and the second cavity, wherein the at least one additional port is separate from the first port and the second port.

5. The arrangement according to claim 1, wherein the sensor comprises at least one detector configured to acquire a signal indicative of one or more patient physiological parameter.

6. The arrangement according to claim 1, wherein the sensor holder is connectable to separate fasteners, wherein each fastener is fastened to different ears.

7. The arrangement according to claim 1, wherein the at least one fastener extends around the subject's ear.

8. The arrangement according to claim 1, wherein the second length of the at least one fastener is configured to extend around the subject's ear.

9. The arrangement according to claim 1, wherein the first length of the at least one fastener is configured to join the second length of the at least one fastener to the sensor holder.

10. The arrangement according to claim 1 comprising:
    at least two fasteners, wherein each of the at least two fasteners is connected to the sensor holder and is configured to fasten the sensor holder to both ears of the subject, wherein each of the at least two fasteners comprises a first length that is substantially inelastic and a second length that is stretchable.

11. An arrangement for fastening at least one sensor to a face of a subject to acquire a signal indicative of one or more patient physiological parameter, the arrangement comprising:
    a sensor holder configured to hold the at least one sensor; and
    at least one fastener connected to the sensor holder and configured to fasten the sensor holder to an ear of the subject, the at least one fastener comprising a first length that is substantially inelastic and a second length that is stretchable, the second length configured to encircle the ear of the subject and to form a loop.

12. The arrangement according to claim 11, wherein the sensor holder and the sensor form an integral structure.

13. The arrangement according to claim 11, wherein the second length of the at least one fastener comprises a first end and a second end, wherein the first end and the second end are connected to the first length of the at least one fastener.

14. A measuring assembly comprising:
 a sensor configured to acquire a signal indicative of one or more physiological parameters of a subject;
 a sensor holder configured to hold the sensor, wherein the sensor is detachable from the sensor holder; and
 at least one fastener connected to the sensor holder and configured to fasten the sensor holder to an ear of the subject, the at least one fastener comprising a first length that is substantially inelastic and a second length that is stretchable.

15. The measuring assembly according to claim 14, wherein the sensor holder also comprises:
 a first cavity comprising a first port configured to allow a first respiration gas flow;
 a second cavity comprising a second port configured to allow a second respiration gas flow; and
 at least one additional port configured to remove the respiration gas flows coming from the first cavity and the second cavity, wherein the at least one additional port is separate from the first port and the second port.

16. The arrangement according to claim 14, wherein the second length of the at least one fastener is configured to encircle the ear of the subject and to form a loop.

17. The arrangement according to claim 14, wherein the second length of the at least one fastener comprises a first end and a second end, wherein the first end and the second end are connected to the first length of the at least one fastener.

18. The measuring assembly according to claim 14, wherein a signal indicative of one or more patient physiological parameter is a signal indicative of respiratory functions.

\* \* \* \* \*

UNITED STATES PATENT AND TRADEMARK OFFICE
CERTIFICATE OF CORRECTION

PATENT NO.        : 8,746,090 B2                                   Page 1 of 1
APPLICATION NO.   : 13/017086
DATED             : June 10, 2014
INVENTOR(S)       : Haveri et al.

It is certified that error appears in the above-identified patent and that said Letters Patent is hereby corrected as shown below:

In the Specification:

In Column 2, Line 19, delete "features." and insert -- features, --, therefor.

In Column 2, Line 60, delete "sensor 1" and insert -- sensor 2 --, therefor.

In Column 4, Line 29, delete "sensor holder 1" and insert -- sensor holder 9 --, therefor.

In Column 5, Line 35, delete "first response" and insert -- fast response --, therefor.

In Column 5, Line 40, delete "port 31," and insert -- port 31. --, therefor.

In Column 7, Line 14, delete "lip no" and insert -- lip so --, therefor.

In the Claims:

In Column 10, Line 7, in Claim 16, delete "arrangement" and insert -- measuring assembly --, therefor.

In Column 10, Line 10, in Claim 17, delete "arrangement" and insert -- measuring assembly --, therefor.

Signed and Sealed this
Twenty-third Day of September, 2014

Michelle K. Lee
*Deputy Director of the United States Patent and Trademark Office*